United States Patent
Ito et al.

(10) Patent No.: US 9,535,069 B2
(45) Date of Patent: Jan. 3, 2017

(54) METHOD OF MEASURING CANCER RELATED SUBSTANCES BY RAMAN SPECTROSCOPY

(71) Applicant: MYTECH CO., LTD., Hyogo (JP)

(72) Inventors: Hiroaki Ito, Tokyo (JP); Yuki Hasegawa, Hyogo (JP); Katsuyuki Hasegawa, Hyogo (JP)

(*) Notice: Subject to any disclaimer, the term of this patent is extended or adjusted under 35 U.S.C. 154(b) by 0 days.

(21) Appl. No.: 14/933,213

(22) Filed: Nov. 5, 2015

(65) Prior Publication Data
US 2016/0187344 A1 Jun. 30, 2016

Related U.S. Application Data

(63) Continuation of application No. PCT/JP2014/062318, filed on May 8, 2014.

(30) Foreign Application Priority Data

May 8, 2013 (JP) .................................. 2013-098608

(51) Int. Cl.
| G01J 3/44 | (2006.01) |
| G01N 33/574 | (2006.01) |
| G01N 33/543 | (2006.01) |
| G01N 33/553 | (2006.01) |
| G01N 21/65 | (2006.01) |

(52) U.S. Cl.
CPC ...... *G01N 33/57496* (2013.01); *G01N 21/658* (2013.01); *G01N 33/5438* (2013.01); *G01N 33/553* (2013.01)

(58) Field of Classification Search
CPC .............. G01J 3/02; G01J 3/44; G01N 21/65; G01N 21/658; G01N 2021/656; G01N 33/574

See application file for complete search history.

(56) References Cited

U.S. PATENT DOCUMENTS

| 6,143,529 A | 11/2000 | Lapidus et al. |
| 9,006,458 B2 * | 4/2015 | Chang ................ A61K 49/0065 548/527 |
| 2004/0259101 A1 | 12/2004 | Shuber |

FOREIGN PATENT DOCUMENTS

| JP | 2007-525662 | 9/2007 |
| JP | 2009-014491 | 1/2009 |

(Continued)

*Primary Examiner* — Abdullahi Nur
(74) *Attorney, Agent, or Firm* — IP Business Solutions, LLC

(57) ABSTRACT

A method for measuring cancer related substances including cancer cell-derived free DNA by Raman spectroscopy, involving steps for preparing a biochip having a meso-crystal region of silver oxides containing a silver peroxide, adding a blood serum or a biological sample solution dropwise onto the meso-crystal region of said biochip, selectively trapping the cancer-related substances having a positive charge in the sample, irradiating the trapped cancer-related substance with an exciting laser light and detecting a surface enhanced Raman scattering therefrom, wherein cancer diseases are evaluated on the basis of the intensity of the Surface Enhance Raman Scattering (SERS). In the carbon-specific D band and G band in the Raman scattering spectrum, a characteristic peak spectrum of the cancer-related substance can be detected in the proximity of the methyl group characteristic of 2900 $cm^{-1}$.

3 Claims, 19 Drawing Sheets

(56) References Cited

FOREIGN PATENT DOCUMENTS

| JP | 2011-81001 | 4/2011 |
| JP | 2013-133475 | 7/2013 |
| WO | 2008/090930 | 7/2008 |
| WO | 2010/101209 | 9/2010 |
| WO | 2012/033097 | 3/2012 |
| WO | 2013/065747 | 5/2013 |

* cited by examiner

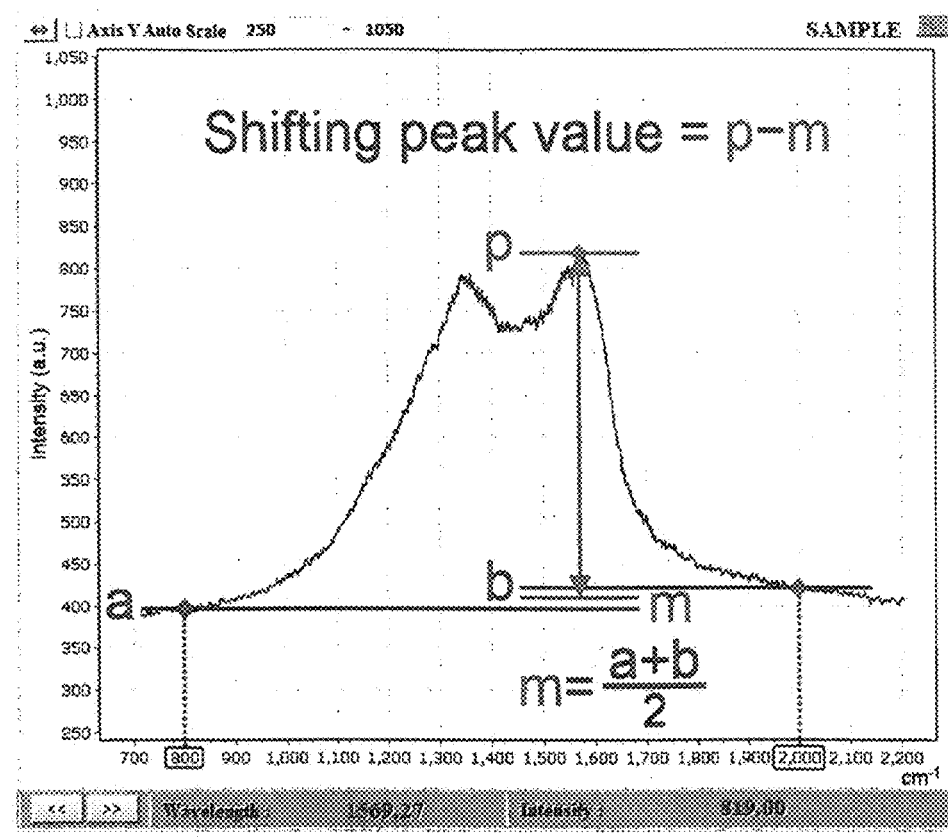
Fig.1 Method of calculating peaks of Raman wave

Fig.8
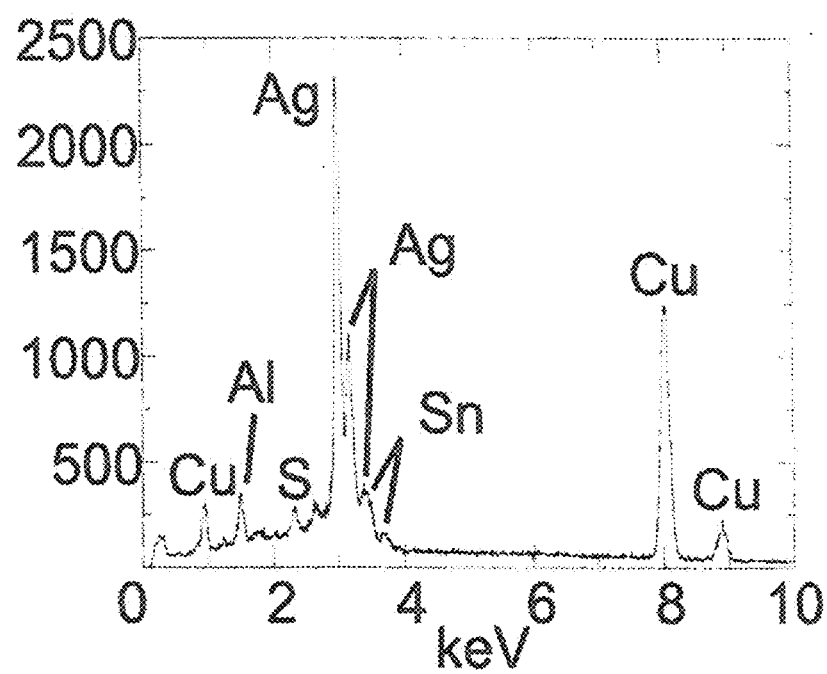
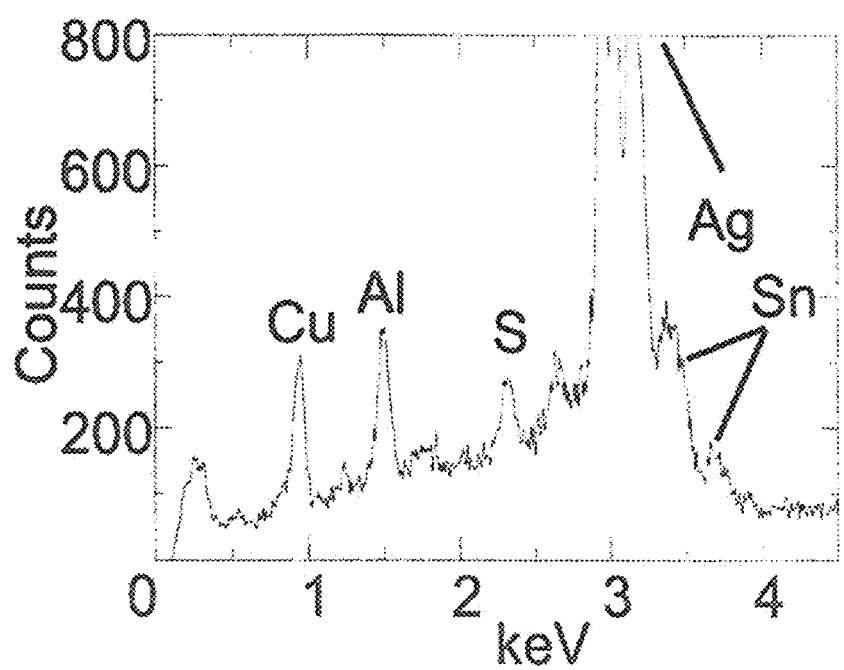

METHOD OF MEASURING CANCER RELATED SUBSTANCES BY RAMAN SPECTROSCOPY

CROSS-REFERENCE TO RELATED APPLICATIONS

This application is a continuation application of Patent Cooperation Treaty Application No. PCT/JP2014/062318, filed on May 8, 2014, which claims priority to Japanese Patent Application No. 2013-098608, filed on May 8, 2013, and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Field of the Invention (Technical Field)

The present invention relates to a method of measuring cancer-related substances which increases in blood with the progress of cancer, including mainly a free DNA (DNA wrapped around the histones) as a target to be measured by Raman spectroscopy.

Description of Related Art

A method of measuring a cancer-related substance which increases in the blood with the progress of the disease has hitherto been used as a diagnostic method for cancer. The cancer-related substances referred to proteins and the like, which are cancer-specific substances extracted from a body fluid of cancer patients and are generally released into the blood when the cancer cells are destroyed. According to the prior diagnostic methods of the cancer, it is determined that there is a possibility that the test subject or patient is suffering from cancer when more than a determined value of the cancer-related substance is found existing in the blood.

Thus as the cancer-related substance released into the blood by destruction of the cancer cells, it is known that not only proteins but also DNA may be released into the blood. And, when compared with the healthy subjects and cancer patients, it has been reported that the amount of the free DNA (ctDNA) derived from cancer cells in blood, is significantly more in those cancer patients than healthy individuals. Thus, by quantifying the free DNA of cancer cells from the body fluid such as blood, it is considered to be able to diagnose the presence of cancer. As such a method of cancer diagnosis, for example, there are proposed 1) a method of diagnosing a possibility of cancer in case of detecting 200 bp or more of DNA to be amplified by the polymerase chain reaction (PCR) method and the like, in the body fluid or feces discharged from the body, and further analyzing a mutation in its DNA if necessary (Patent Document 1 and 2), and 2) a method of quantifying genomic DNA contained in a body fluid, and further performing DNA testing in the case of more than a predetermined value of the genomic DNA (Patent Document 3).

Furthermore, even if the patient is diagnosed suffering from cancer, mere quantitative analysis of the DNA in body fluids is unable to identify a cancer suffering organ. When the cancer is arising and progressing, it is known that a specific mutation of DNA occurs depending on the original cancer site. Therefore, by clarifying the type of mutation in the DNA, it may be possible to identify an organ or a cancer site where the cancer is developing. Here, as Mutations of DNA, there are listed point mutations of DNA and also structural abnormalities such as chromosome gain or loss. For example, in about 70% of pancreatic cancer, it is known that the point mutation occurs in the K-ras gene. Also, in the analysis of loss of heterozygous, (hereinafter referred to as LOH) there have been reported the loss of specific chromosomal arms depending on each cancer type, for example, it is known that LOH is concentrated on the short arm of chromosome 3 in case of the lung cancer. Also, the amplification of long arm No. 8 of chromosome and the amplification of RB2 are known in the breast cancer, Therefore, in order to provide an improved method for diagnosing cancer with high accuracy by quantifying the free DNA from cancer cells with a biochip as described herein, there has been provided a method of diagnosing cancer, which comprises a step of extracting a free DNA from plasma collected from a subject, a step of calculating the free DNA per unit volume of the extracted plasma by quantifying the free DNA, a step of comparing the calculated value of the free DNA with a second threshold value more than the first threshold value, a step of making a diagnose as follows; the subject has a high possibility of affection with cancer when the calculated value is less than the first threshold value, while some DNA from normal cells are mixed in the plasma when the above threshold is more than the second threshold value (patent document 4).

THE PRIOR TECHNICAL ART

Patent Literature

Patent document 1: U.S. Pat. No. 6,143,529
Patent document 2: US Pat. Pub. No. 2004/0259101 A1
Patent document 3: WO 2008/090930
Patent document 4: Japanese Patent Publication No. 2011-81001

However, for example, even if one tried to quantify the free DNA derived from cancer cells in a whole blood, whereas a trace amount of the free DNA is contained therein, a large amount of the DNA comes from the lymphocytes derived from normal cells. Accordingly, even if DNA can be directly extracted from a whole blood, it is difficult to quantify the free DNA derived from cancer cells exactly. Therefore, for example, by using a plasma that has been separated from the whole blood, it is considered to provide a method of quantifying the free DNA derived from the cancer cells in the plasma, but depending on the extraction method of DNA, the DNA derived from the normal cells from such as lymphocytes might be incorporated with the free DNA derived from the cancer cells, so that not only the free DNA derived from the cancer cells but also the DNA derived from the normal cells are to be qualified together, resulting in a cause for erroneous diagnosis of cancer. Therefore, in proceeding an accurate diagnosis of cancer, it is important to accurately quantify the free DNA (hereinafter referred to the DNA wound around the histones in the present invention) derived from cancer cells, so that it is necessary to provide how to extract the free DNA simply and rapidly and how to remove the DNA from normal cells in order to improve the detection accuracy of the free DNA derived from cancer, and also how to detect a trace amount of DNA precisely for the appropriate diagnosis of cancer.

Raman spectroscopy has been used for analyzing a trace amounts of DNA in the blood, and is promising for qualitative and quantitative detection tools, but SERS phenomena is not only, 1) the mechanism is not understood perfectly, but also 2) it is exactly difficult to synthesis and control a structurally defined nano-materials for SERS, 3) there are a lot of the problems to be solved from the aspect of reproducibility and reliability due to change of the enhanced efficiency by the polarization direction and the wavelength of an exciting light used at the time of measuring the spectrum, which remains as a big problem for the application of SERS phenomena, including the development and commercialization of the biosensor. Therefore, a hybrid structure of the nano-wires and nano-particles has been proposed in order to enhance SERS signals of biological extracts, proteins and bio-molecules such as DNA and to improve the reproducibility, the sensitivity and the reliability of the measurement of SERS signals (Patent Document 4). However, the hybrid structure of the nano-wires and the nano-particles is used for trapping the object to be measured via some receptors, so that it is not still appropriate as a method of detecting a trace amount of the free DNA from the cancer cells.

BRIEF SUMMARY OF THE INVENTION

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 1 shows a method of calculating peaks in the Raman wave, in which spectra of the Raman scattering by 633 nm laser of human serum samples indicates the formation of a peak of scattering intensity in the vicinity of 1350 $cm^{-1}$ and around 1550 $cm^{-1}$.

FIG. 8 is a graph showing a result of EDS spectra analysis of quantum crystals (elemental analysis).

DETAILED DESCRIPTION OF THE INVENTION

Figure 2A:
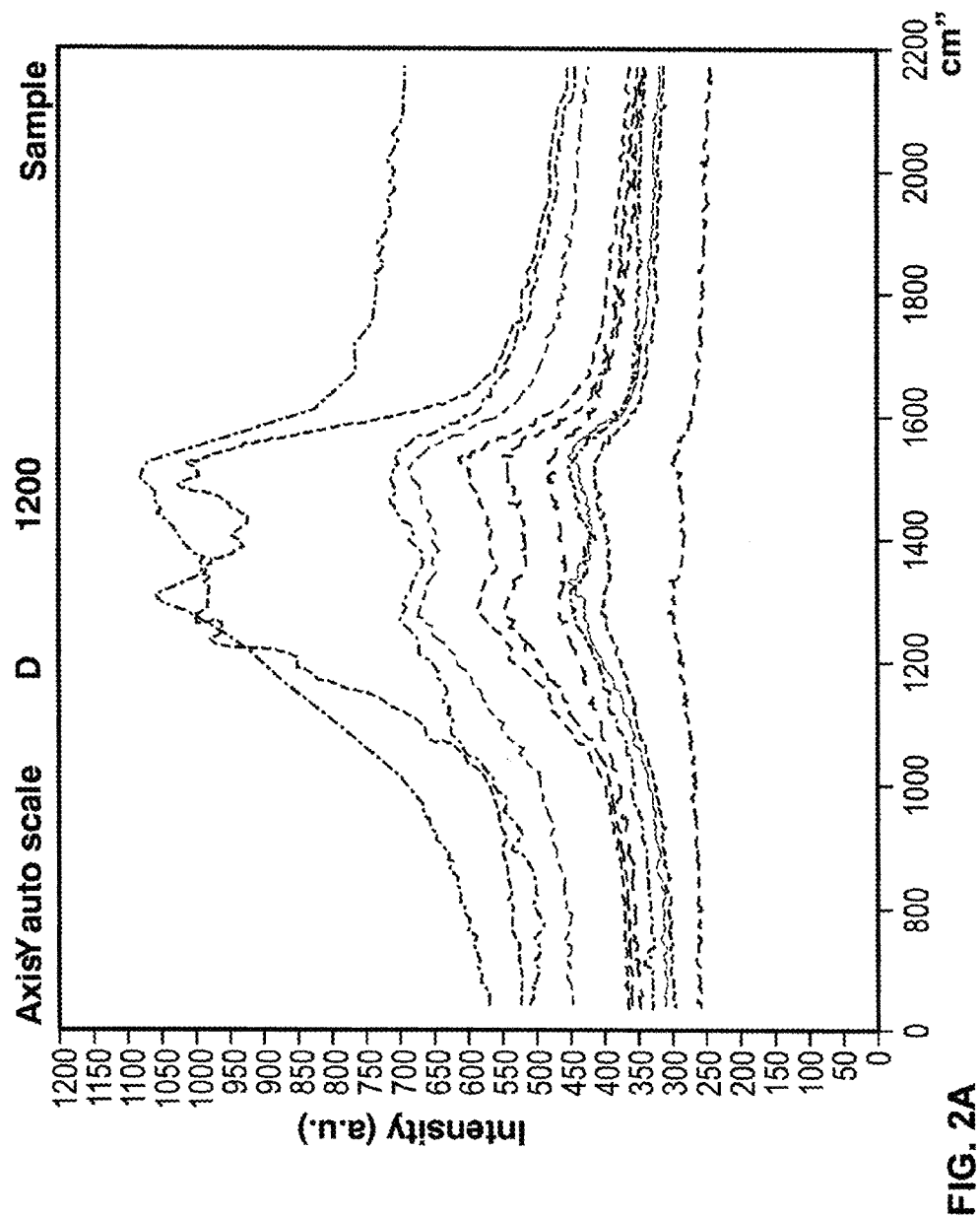
FIG. 2A is a Raman spectral diagram of a sample by adjusting the sera obtained from 12 cases of stomach cancer patients.
Figure 2B:
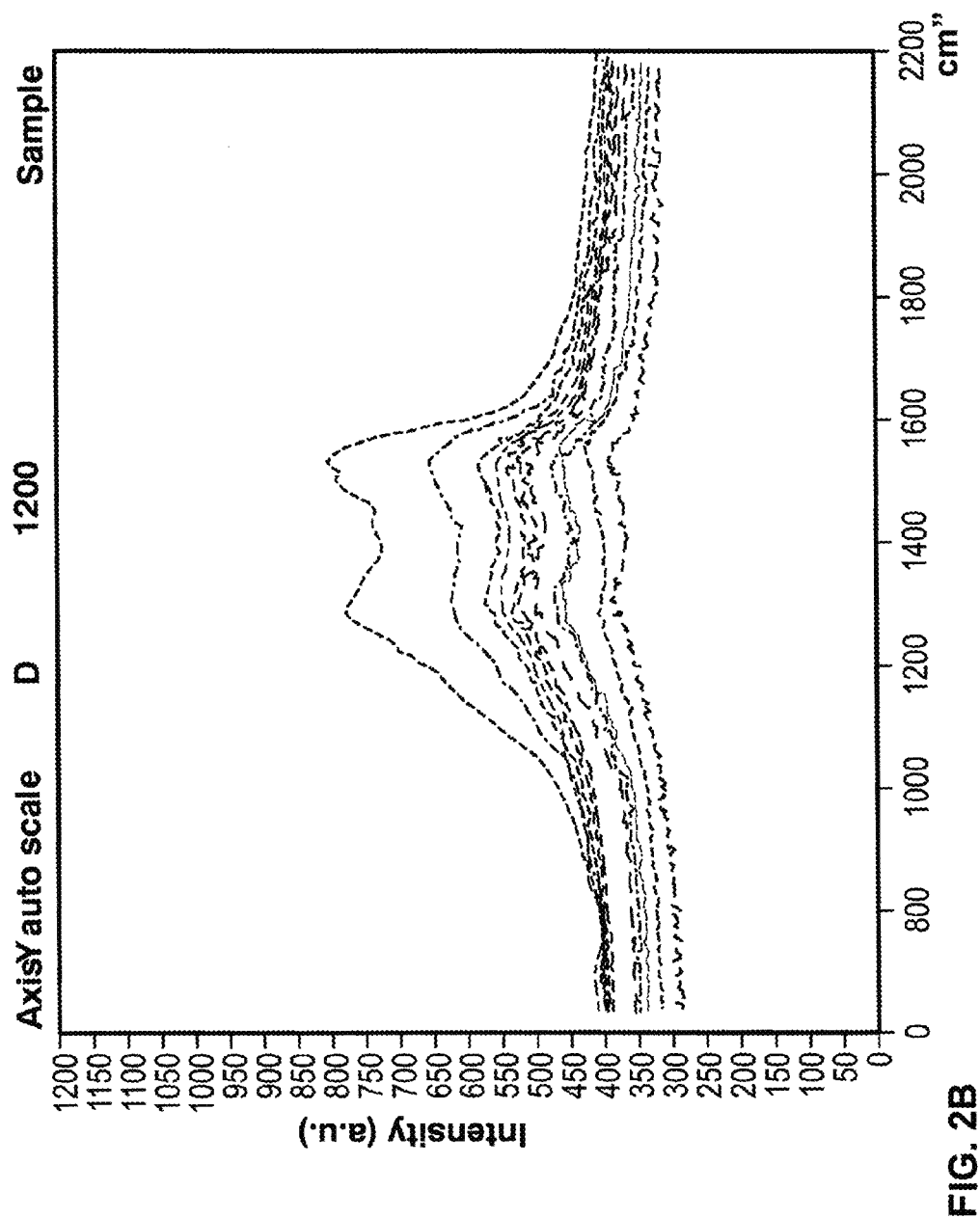
FIG. 2B is a Raman spectral diagram of a sample by adjusting the sera obtained from 12 cases of colorectal cancer patients.
Figure 2C:
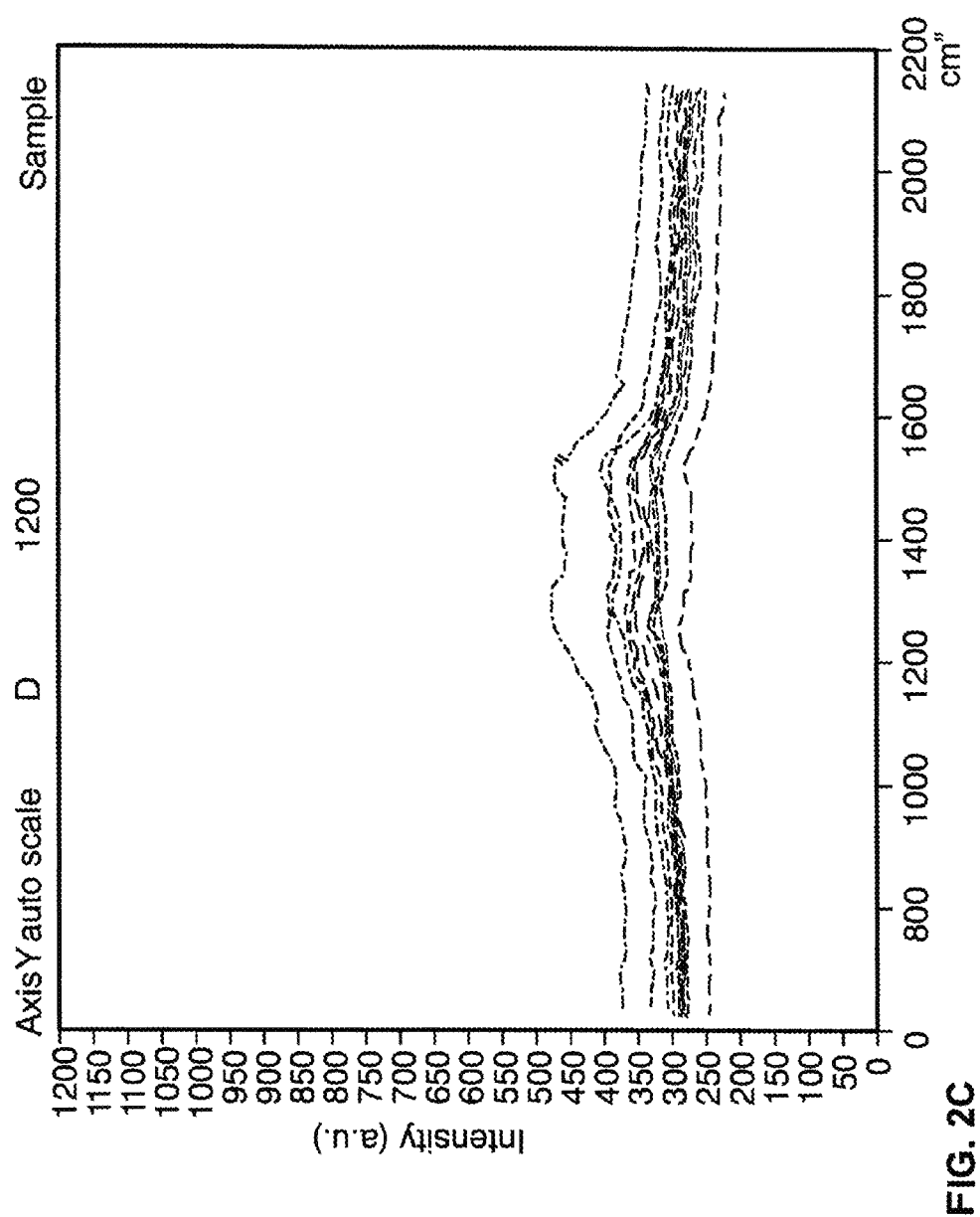
FIG. 2C is a Raman spectral diagram of a sample by adjusting the sera obtained from 12 cases of benign disease patients.
Figure 2D:
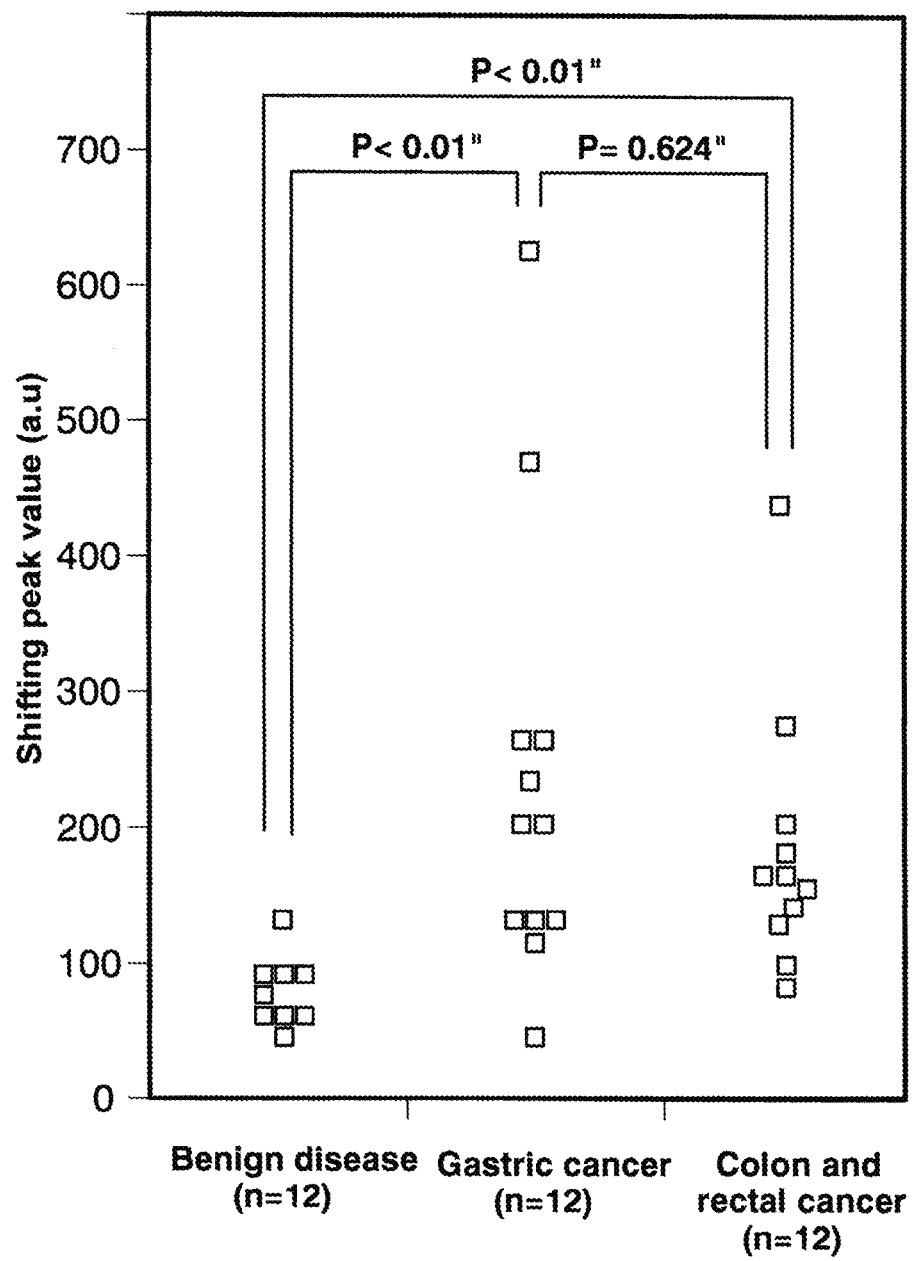
FIG. 2D is a graph showing a comparison of Raman scattering peak rising value of stomach cancer, colorectal cancer, and benign disease sample.

After research considering the above problems, the present inventors have found that the necessary target to be directly detected should the cancer related substances such as the free DNA derived from cancer cells, which increase in blood with progress of the cancer when the cancer is susceptible and it is considered best to detect directly the free DNA without using any receptors.

Here, the free DNA to be detected is a DNA wound around the protein called histones, which wound unit structure (1 set) is called a nucleosome and the structure which comes to a string shape of nucleosome gathered is called a chromatin (fibers). When the cells are in a cancerous state and divide repeatedly, DNA becomes wrapped around the histone so as not to come out of the genes (tumor suppressor gene) inconvenient to increase of the cancer and the DNA winding onto the histone becomes wound more tightly by methylation so as not to make the DNA loosen from the histones easily. Usually the histones are charged as (+), while the DNA is charged as (−), so that the two are stuck together magnetically and the methylation makes the two not to be untied easily where the methylated DNA wound around the histones is charged to the (+) state (see FIG. 11 (*a*)). On the other hand, acetylation makes histone change into charge (−), so that DNA of (−) comes to act repulsively to the histones changed into the (−) state by the acetylation, resulting in expression of genes due to the unwound mechanism of the 'thread' of DNA from the histones (see FIG. 11 (*b*)). Therefore, in order to selectively adsorb or trap the free DNA derived from cancer cells as the DNA wound around the histones, the substrate to absorb or trap the cancer related substances (+) in the sample is preferably considered to have a state of charge (−) in the sample for analysis.

Meanwhile, the present inventors have found that, on a metal substrate having a less noble electrode potential (large ionization tendency) than that of a metal forming a metal complex in the metal complex aqueous solution, an electrochemical reduction occurs due to the electrode potential difference between the metal substrate and the metal complex, resulting in deposition and aggregation of the metal complex from the aqueous solution onto the metal substrate to form quantum crystals (nano-sized metal complex crystals). In case of silver complex, the silver complex can be formed as quantum crystals of silver complex due to an electro-chemical reduction on copper or copper alloy of less noble electrode potential (large ionization tendency) than that of silver in a silver thiosulfate aqueous solution. Specifically, the concentration of the metal complex in the aqueous solution should be determined by considering the size of the quantum crystals to be formed mainly and, where a dispersing agent is used, its concentration has to be considered. While the complex concentration can be usually used from 100 ppm to 5000 ppm, 500 to 2000 ppm of such concentration is preferably used in order to prepare nano-sized crystals called a nano-cluster depending on the functionality of the ligand. Metal complex to be formed as a quantum crystal may be selected to have a complex stability constant (log β) of the formula (I) correlating with the electrode potential E of the substrate metal.

$$E° = (RT/|Z|F)) \ln(\beta i) \qquad \text{Formula(I):}$$

where E° is the standard electrode potential, R is the gas constant, T is the absolute temperature, Z is the ion valence, F represents the Faraday constant.

If the metal complexes are selected from the group consisting of plasmon metals such as Au, Ag, Pt and Pd, the plasmon metals have a function of localized surface plasmon resonance enhancement effect for the Raman light. In particular, when the metal complex is a silver complex, the complex may be formed by reaction of silver complexing agent having a stability constant (formation constant) (log (βi) of 8 or more with a silver halide, where a silver halide may be preferably selected as the halides and the complexing agent may be preferably selected from the group consisting of thiosulfate salt, thiocyanate salt, sulfite salt, thiourea salt, potassium iodide salt, thiosalicylic acid salt, and thiocyanuric acid salt. In case of silver complex, the resulting quantum crystal has quantum dots made of nano-cluster having an average diameter of 5~20 nm, so that the size of the quantum crystal will be in a range of 100~200 nm.

Figure 9:
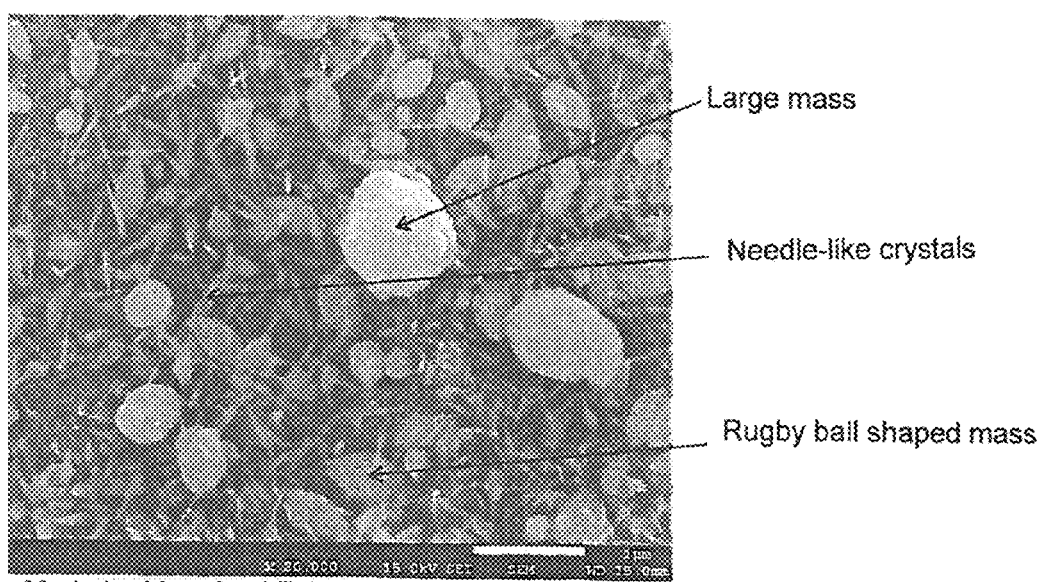
FIG. 9 is a photograph showing SEM image of quantum crystals alkali-treated in the presence of a halogen ion (Sodium hypochlorite treatment).
Figure 10A:
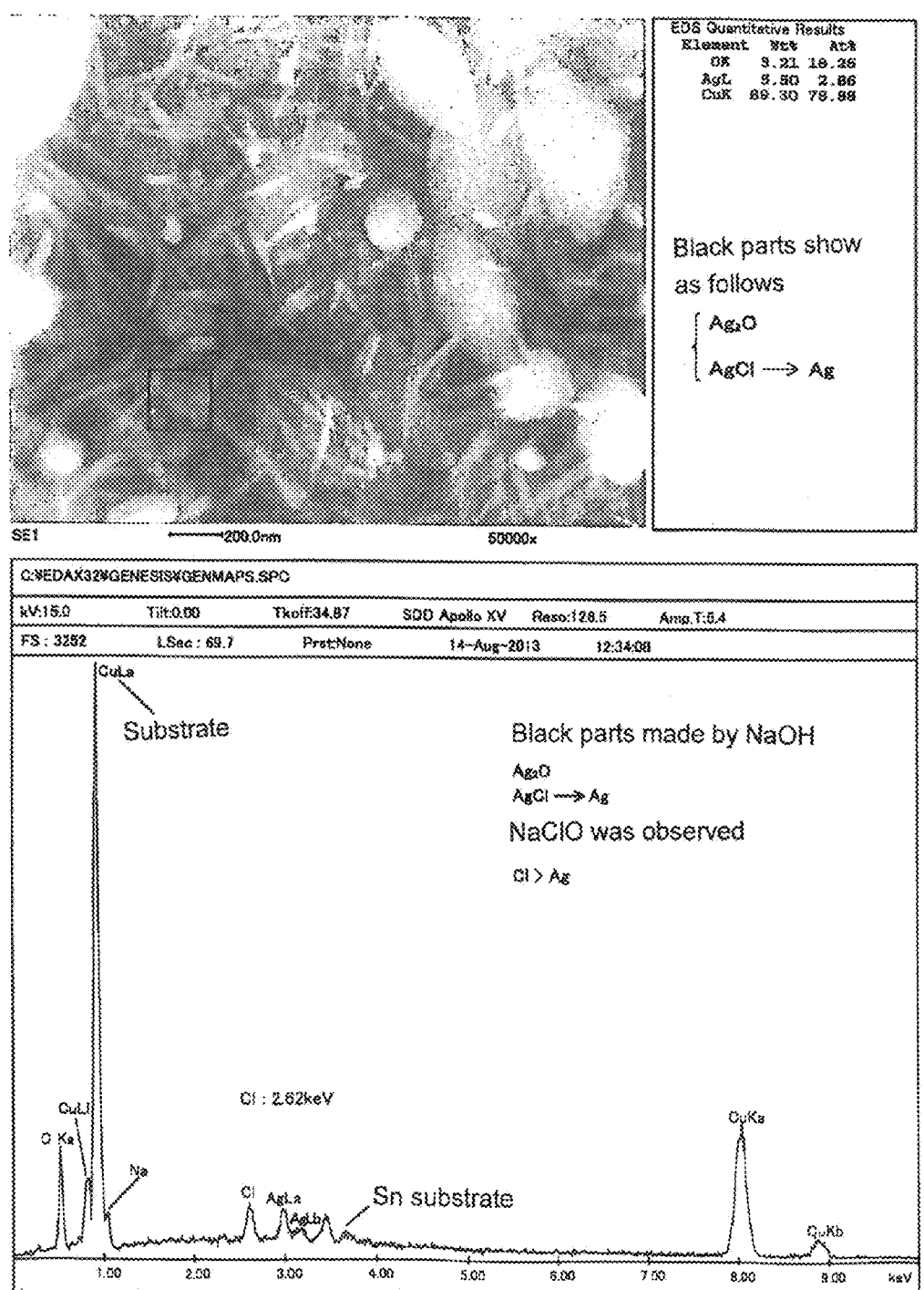
FIG. 10A is a photograph showing needle-like crystals of the alkali-treated quantum crystals.
Figure 10B:
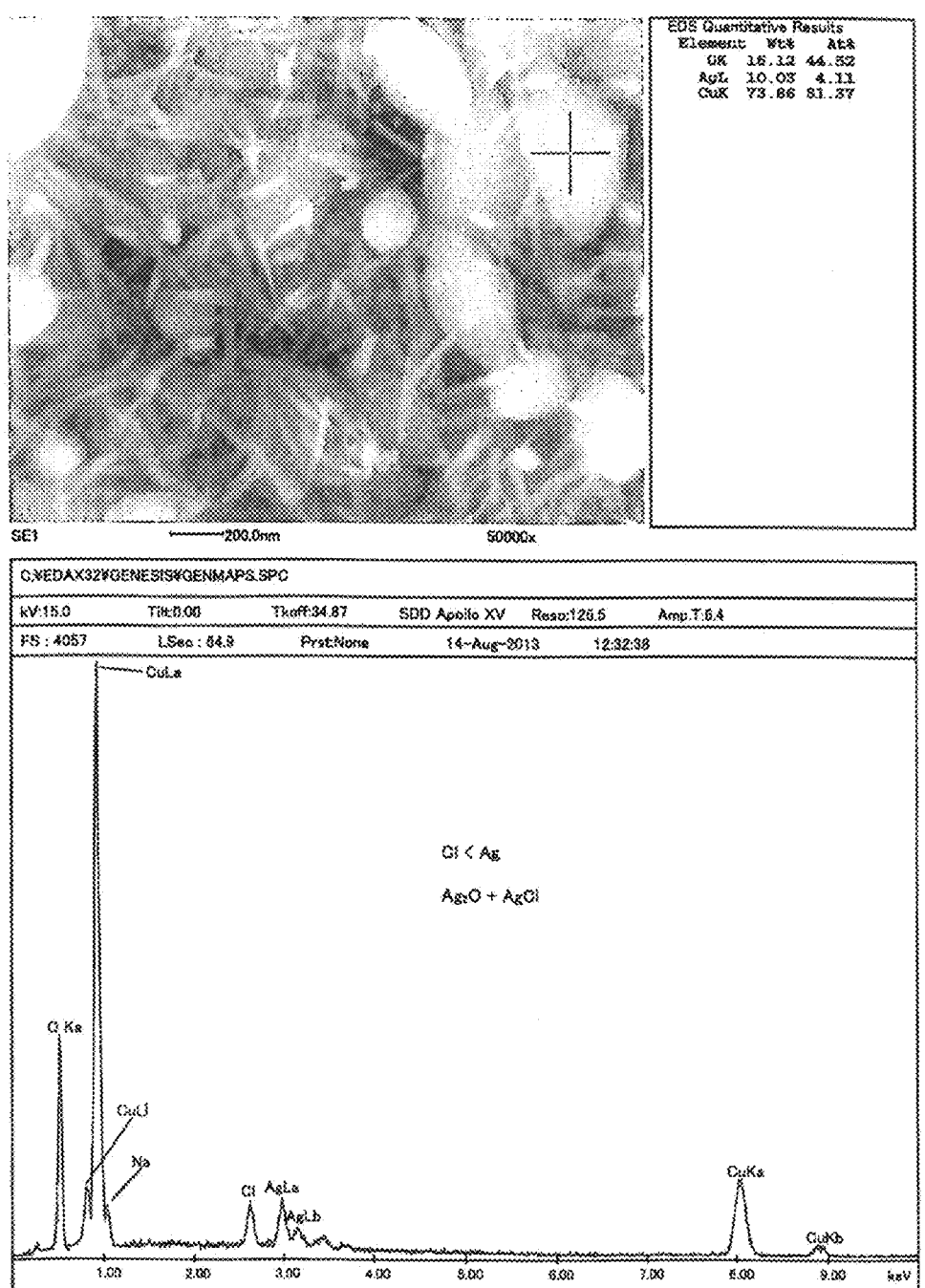
FIG. 10B is a photograph showing a rugby ball-shaped mass in the. needle-like crystals.
Figure 10C:
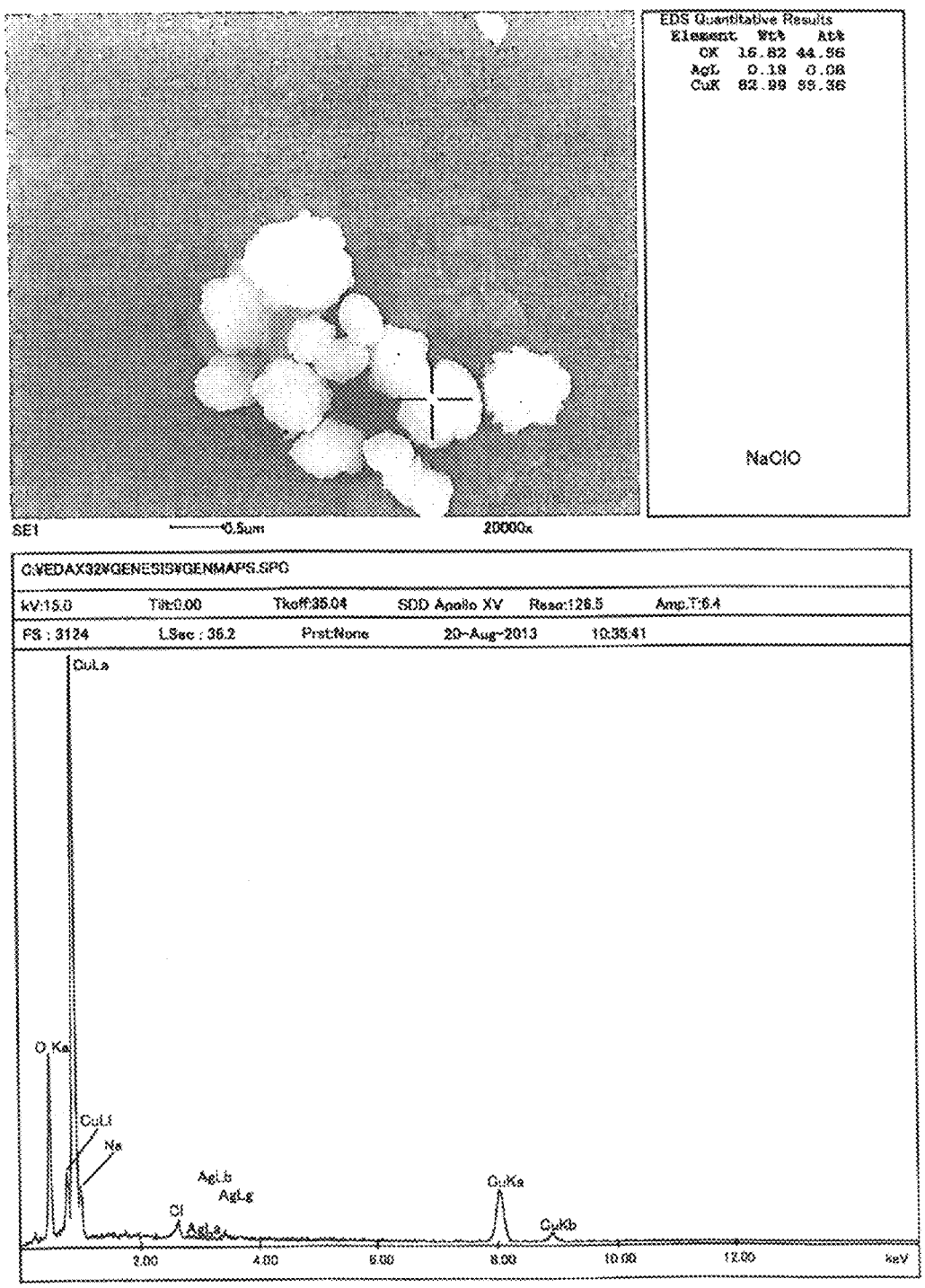
FIG. 10C is a graph showing a result of EDS spectra of large mass (elemental analysis).
Figure 11:
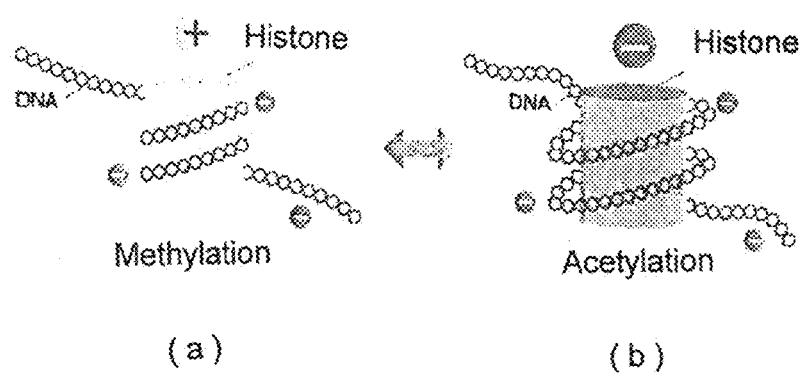
FIG. 11 is functional illustration views showing a state of the methylated free DNA (a) and a state of acetylated DNA (b).

The inventors of the present invention have found that such silver complex can be changed by means of alkali treatment in the presence of halogen ions (for example treatment with sodium hypochlorite) according to the following reaction into nano-crystals of silver oxides composite comprising a silver peroxide and silver halide as cores (see FIG. 9), which shows the (−) charge in water while the DNA wound around the histones shows the (+) charge (FIG. 11 (*a*)), so that the cancer related substance represented by the free DNA having a positive charge was found to selectively be adsorbed. The inventors of the present invention have also found that the acicular nano-crystals of silver oxides composite containing a silver peroxide can be reduced by irradiation of an exciting laser beam, into a metallic silver, results in that the metallic silver shows the surface plasmon enhancement effect by the laser beam irradiation, and thereby the cancer related substances represented by the trapped free DNA becomes to be able to be detected by Surface Enhanced Raman Scattering (SERS).

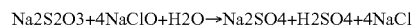

Na2S2O3+4NaClO+H2O→Na2SO4+H2SO4+4NaCl

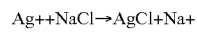

Ag++NaCl→AgCl+Na+

Ag++3NaOCl→2AgCl+NaClO3+2Na+

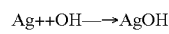

Ag++OH—→AgOH

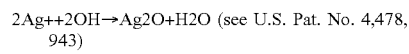

2Ag++2OH→Ag2O+H2O (see U.S. Pat. No. 4,478, 943)

The present invention is based on the above findings and is intended to provide a bio-chip for measuring cancer related substances, which bio-chip is provided with a region containing a composite of acicular nano-crystals of silver oxide comprising silver halide or halogen, which has properties for showing a negative charge (−) in water in order to adsorb cancer related substances having a positive charge (+) and form a charge transfer complex therefrom. On the other hand, the composite of acicular nano-crystals of silver oxide can be changed into metallic silver nano-particles by a laser light irradiation, resulting in making a region where the surface plasmon enhancement effect is obtained by the laser irradiation.

The composite of acicular nano-crystals of the silver oxide according to the present invention, in which silver oxide contains silver peroxides to be self-assembled into a neurons form three-dimensional super-structure (hereinafter called a meso crystal in the present invention) (FIGS. 12 and 13), although an Ag/AgCl electrode is subjected to a controlled-potential electrolysis in a silver ion aqueous solution to get the meso-crystal of silver oxide containing silver peroxides, silver complex quantum crystals. For example, silver thiosulfate quantum crystals are subjected to an alkali treatment with sodium hypochlorite solutions in the presence of halogen ions. to obtain the silver oxide mesocrystals.

According to the present invention, the utilization of the biochip of the present invention brings about such an advantage that the Raman analysis of biological samples containing the blood makes it possible to quantify cancer-related substances, such as the free DNA. Specifically, using the composite needle nano-crystals of silver oxide comprising silver halide or halogen, that is, the biochip having a meso crystal region of the silver oxide containing peroxide of silver (FIGS. 12 and 13), the serum or biological liquid sample is dropped onto the biochip so that the cancer related substances in the serum may be selectively trapped because the cancer related substances have a positive charge in the sample. The Raman scattering from the cancer related substances is subsequently enhanced by the effect of SERS and detected. Therefore, it is possible to determine the cancer disease by the intensity of surface enhanced Raman scattering (SERS).

The cancer related substances in serum include DNA wound around histone derived from cancer cells (referred to as the free DNA in the present invention), a nucleosome of unit structure (1 set) and a chromatin (fibers) which is a string-like structure of nucleosome. Although the serum includes globulin having a positive charge, the increase of globulin is at largest up to two times or less and, since the cancer procession may result in the increase of the cancer-related substances detected by the biochip of the present invention reaching up to 100 times or more, it shows the detection of the increase of the substance (cancer cell originating free DNA). Furthermore, DNA leaving from the normal cells, DNA leaving from histones by acetylation and albumin altogether account for approximately 60% of serum, however, in order to take on a negative charge, they will not be trapped in the practice of the present invention. Therefore, it is advantageous for quantitative examination of the cancer related substances.

Moreover, the needle-like nano-crystals used in the practice of the present invention (meso crystals of silver oxide containing peroxide of silver) tend to be easily negatively charged in an aqueous solution and, therefore, it appears that the meso-crystals according to the present invention may form a charge transfer complex in contact with the target molecules such as cancer related substances. Furthermore, the silver oxide is reduced upon receipt of the light energy to thereby being changed into a metallic silver and, therefore, the surface plasmon resonance enhancement effect peculiar to the regularly arranged metallic nano-particles may occurs on the meso-crystals. Thus, the acicular nanocrystals (meso crystal) of the present invention, although being a non-metal compound, is provided with metal properties and ionization properties concurrently and, therefore, the present invention can provide a suitable biochips for measurement of surface enhanced Raman scattering (SERS).

The metal complex to form a quantum crystal is selected to have a complex stability constant (log β) of the formula (I) to correlate the electrode potential E of the supported metal.

$$E° = (RT/ZF)\ln(\beta i) \quad \text{Formula (I):}$$

where E ° is the standard electrode potential, R is the gas constant, T is absolute temperature, Z is the ion valence, F represents the Faraday constant.)

In the case that the metal complexes are selected from the group consisting of plasmon metals such as Au, Ag, Pt and Pd, the plasmon metals have a function of localized surface plasmon resonance enhancement effect for the Raman light. In particular, when the metal complex is a silver complex, the complex may be formed by reaction of silver complexing agent having a stability constant (formation constant) (log βi) of 8 or more with a silver halide, where a silver halide may be preferably selected as the halide and the complexing agent may be preferably selected from the group consisting of thiosulfate salt, thiocyanate salt, sulfite salt, thiourea salt, potassium iodide salt, thiosalicylic acid salt, and thiocyanuric acid salt. In case of the silver complex, the resulting quantum crystal has quantum dots made of nano-cluster having average diameter of 5~20 nm, so that the size of the quantum crystal will be in a range of 100~200 nm.

The concentration of the metal complex in the aqueous solution should be determined depending on the size of the quantum crystals mainly, and, where a dispersing agent is used, the concentration of the dispersing agent should be considered correspondingly. Typically, although the metal complex in the aqueous solution can be used in the range of 100 ppm to 5000 ppm, the concentration in the range of 500 to 2000 ppm is rather preferred where nano-sized particles called as the nano-cluster is desired to be prepared depending on the functionality of the ligand.

The quantum crystals formed on a metal substrate or metal particles are believed likely to have a positive polarity in an aqueous solution as a metal complex crystals and, in order to allow the protein in a biological sample to be adsorbed, the polarity is preferably adjusted by means of an alkali treatment n the presence of halide ions, for example, by dropping sodium hypochlorite solution of pH 11 or higher thereon. By so doing, the quantum crystals is re-crystallized not only to have a negative polarity in an aqueous solution but also to form the composite needle nano-crystalline comprising silver oxide including peroxides, wherein a sample of cancer related substances derived from the cancer cells with a positively charged is possible to facilitate the immobilization of the free DNA.

Figure 3:
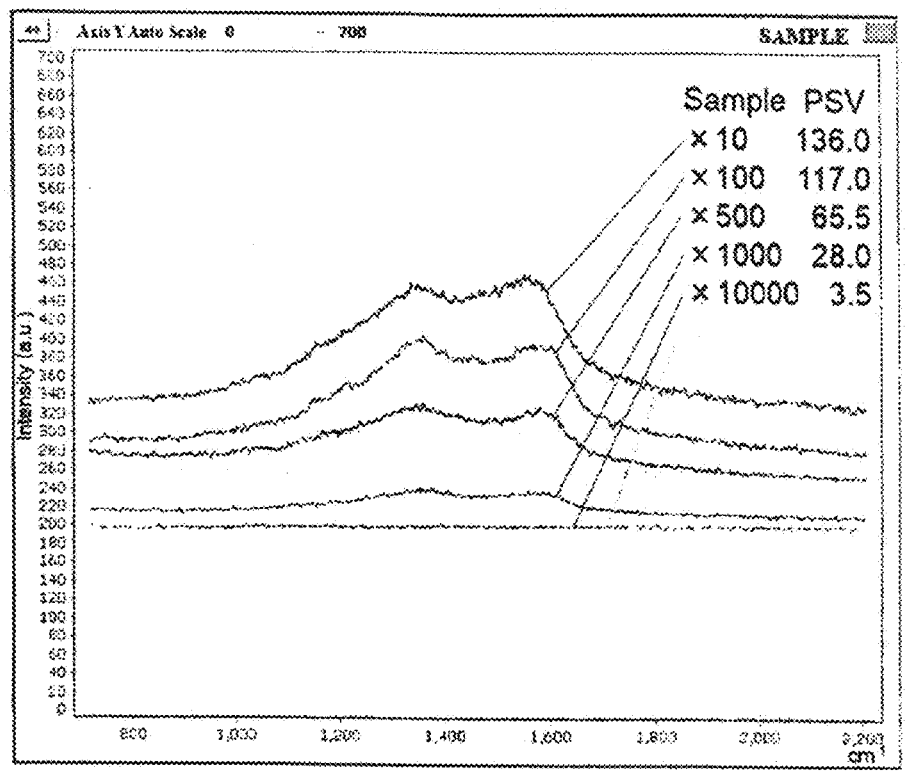
FIG. 3 is the Raman spectrum showing the relationship between diluted samples and the Raman scattering intensity where the diluted samples are obtained from 12 cases of colon cancer patients, which shows that the scattering intensity peak rising value and the sample concentration are correlative each other.

Determination of the total protein concentration in a biological sample can be measured by obtaining the Raman spectrum resulting from irradiation of the laser beam of a specific wavelength. FIG. 3 is a Raman spectrum wherein a serum sample of colon cancer patients is diluted 10-fold, 100-fold, 500-fold, 1000-fold and 10000-fold with pure water and measured by 633 nm laser (30 mW), to obtain peak rising value (PSV) and peak integration value, which change with concentration. Therefore, it will readily be understood that the quantitative analysis of the total protein in the serum can be accomplished. In the Raman spectrum, particular peaks are observed in carbon-specific G band (1300~1400 cm−1 vicinity) and D band (in the vicinity of 1550~1600 cm−1), and a peak can also be observed in the vicinity of −1 specific 2900 cm to methyl group. The observation of the peaks in the Raman spectrum as discussed above appears to suggest that the methylation state of DNA wound around histones could have been detected as a cancer related substances.

Therefore, it is possible to analyze the identification and progress of cancer from information such as the peak height, the peak integral values and the peak onset time of the resulting Raman spectrum. FIG. 1 shows a peak calculation method of Raman waveform, wherein from the spectrum of Raman scattering by 633 nm laser of human serum samples it is confirmed to form the peak of the scattering intensity in the vicinity of 1350 cm$^{-1}$ vicinity and 1550 cm$^{-1}$. Thus, on the basis of average value (m) between 800 cm$^{-1}$ (a) and 2000 cm$^{-1}$ (b) of scattering intensity, the (p-m) peak rising value was defined as (Shifting Peak Value PSV). The entire area of the peak was as the integral value. These peaks rise value and peak integral value are important in view of the cancer related substances in human serum, it is possible to be an indicator of the identification and progression of cancer in conjunction with peak onset time.

Figure 4:
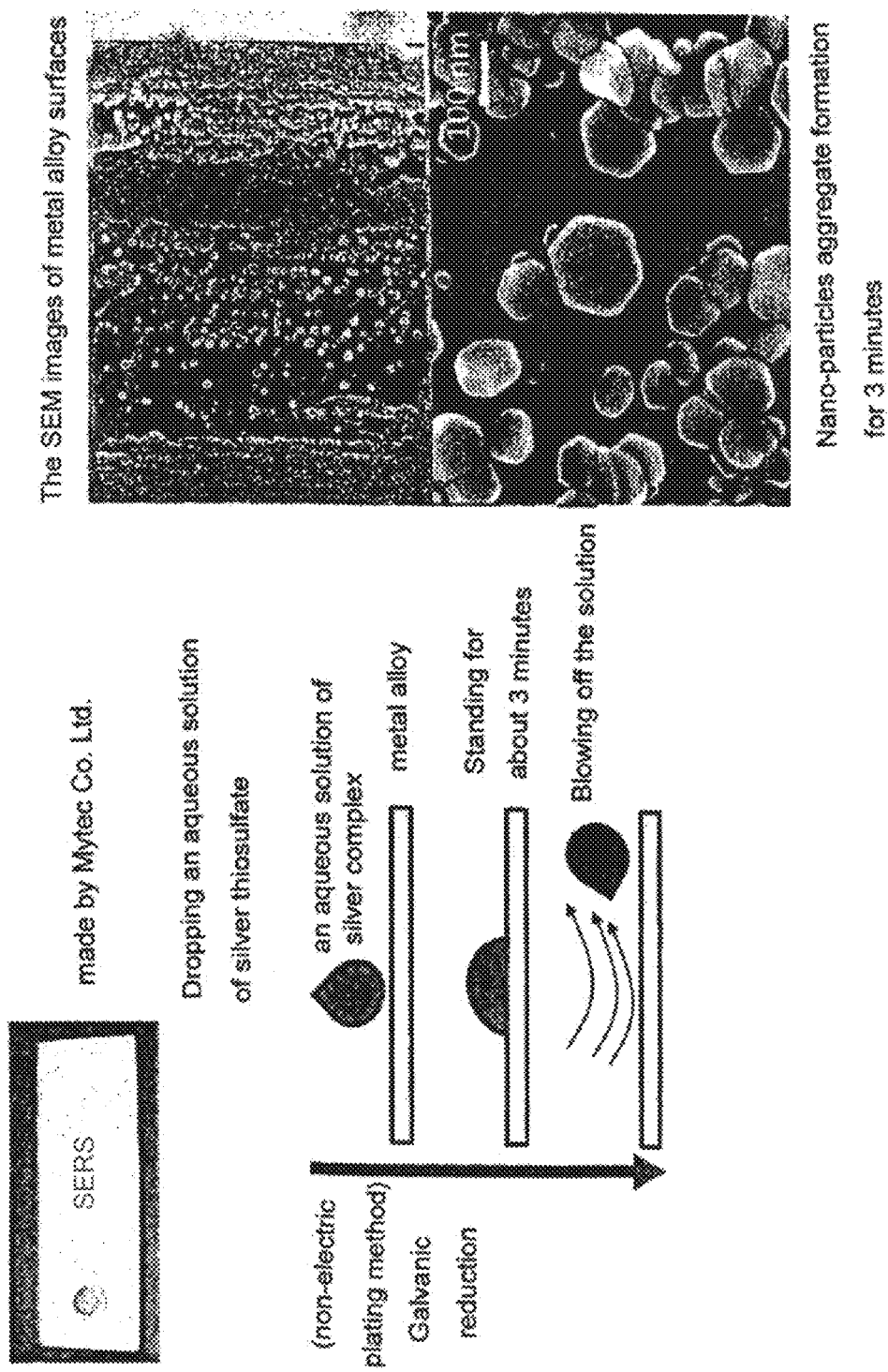
FIG. 4 is an explanatory diagram showing a making procedure of the present inventive new SERS substrate shown in Example 1, wherein an upper left photograph shows a substrate of Mytech Co., Ltd. with the SEM image.

As shown in FIG. 4, an aqueous solution containing 1000 ppm of silver thiosulfate was prepared and the 1 drop was added dropwise onto a phosphor bronze plate. After the phosphor bronze plate with the aqueous solution drop thereon has been left standing for about 3 minutes, the solution on the plate was blown off. On the plate, a quantum crystal was obtained as shown in the SEM image at the right side of FIG. 4.

Figure 5:
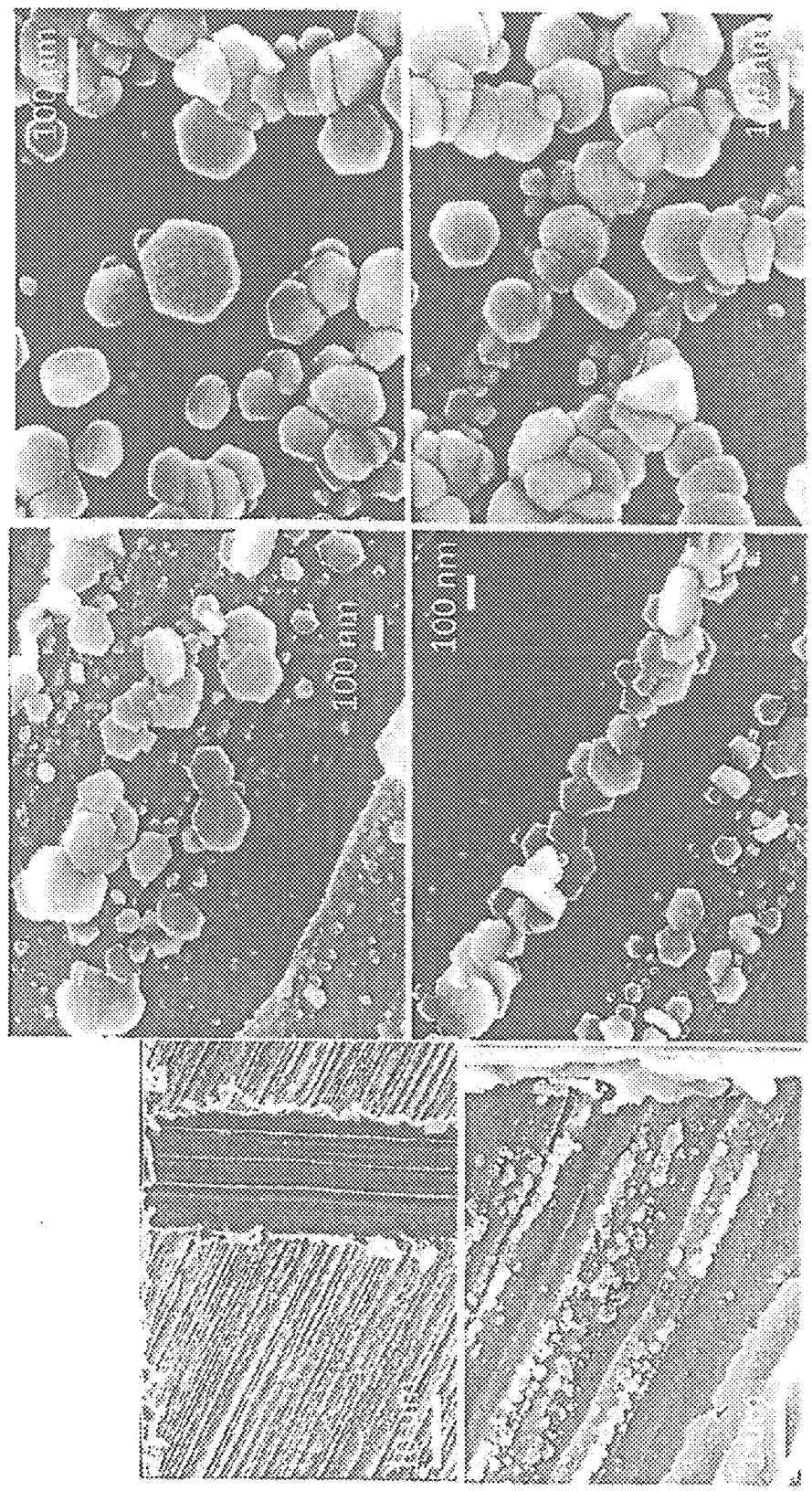
FIG. 5 is a photograph showing various SEM images of the nano-particle aggregate (quantum crystal) prepared in Example 1.
Figure 6:
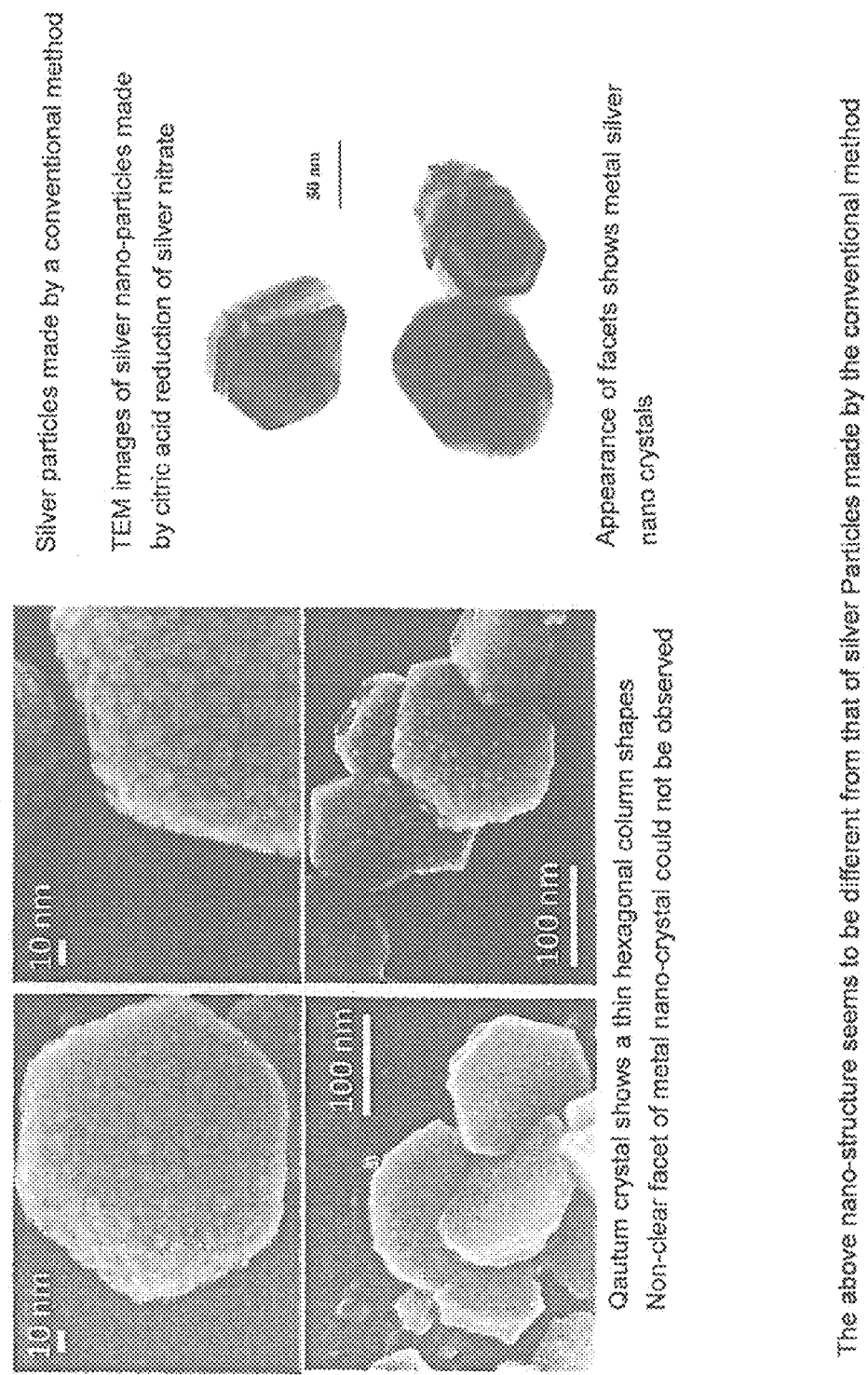
FIG. 6 is a photograph showing an enlarged SEM image of a nano-particle.

FIG. 5 is a photograph showing various SEM images of the nano-particle aggregate prepared in Example 1 (quantum crystal), and FIG. 6 shows an enlarged SEM image of nano-particles where there were thin hexagonal columnar crystals of 100 nm more or less and having an unevenness surface of several nm order. The inventors could not find out any specific facets of metal nano-crystals in the quantum crystals.

Figure 7:
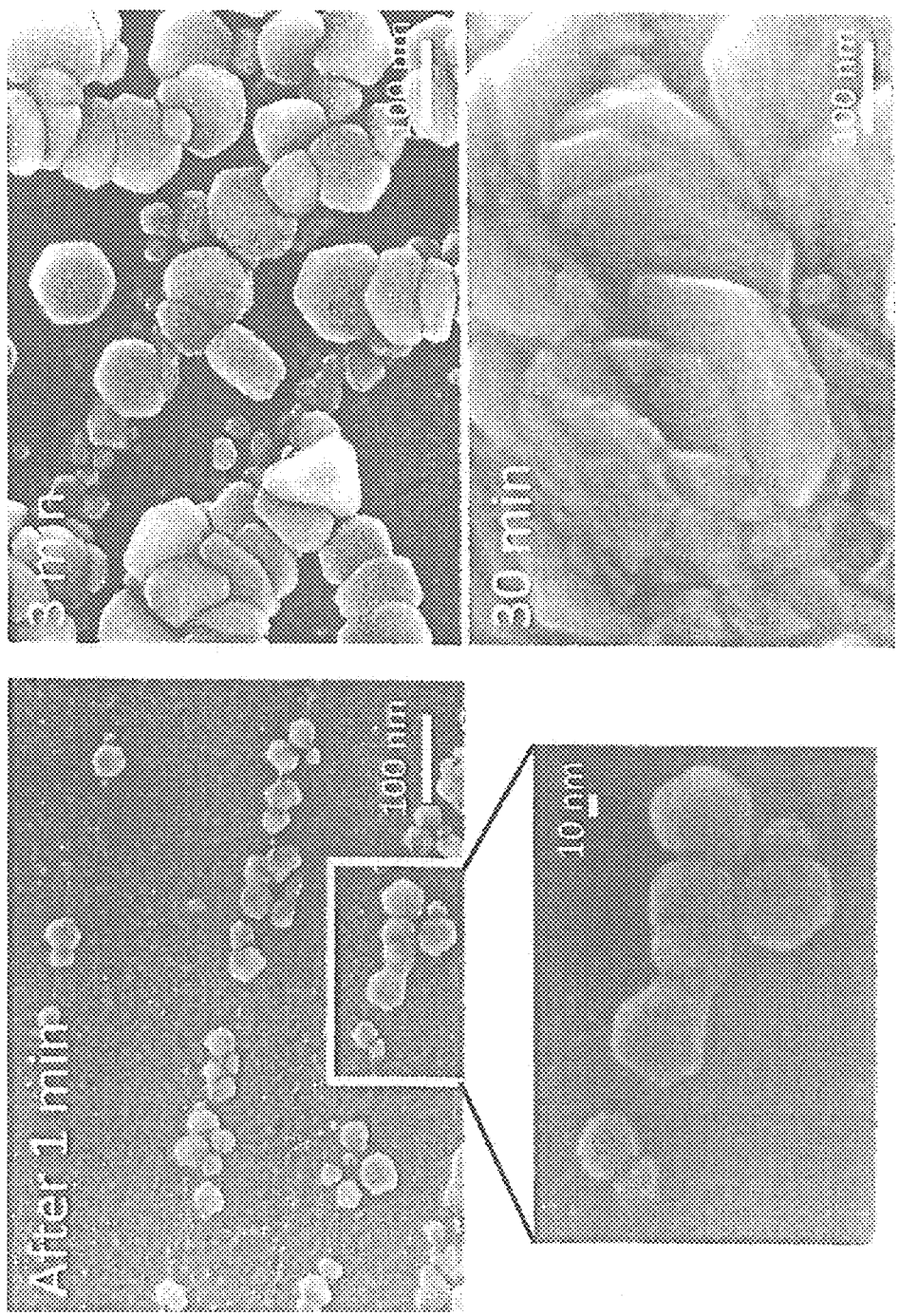
FIG. 7 is a photograph showing the relationship between quantum crystal shapes and standing times after dropping on the phosphor bronze substrate.

FIG. 7 is a microphotograph showing the relationship between quantum crystal shapes and the standing time after dropping onto the phosphor bronze substrate, where it is recognized that firstly, a hexagonal quantum crystal is produced and then growing while maintaining the crystal shape.

FIG. 8 is a graph showing results of EDS spectra (elemental analysis). of the quantum crystals where not only silver but also elements derived from complex ligands can be detected in case of the quantum crystal on the phosphor bronze substrate, while only silver can be detected in the case of the quantum crystals formed on a copper plate by using 1000 ppm of silver thiosulfate in aqueous solution and keeping it for the standing time of 3 minutes after dropping onto the copper substrates.

In the case of 1000 ppm of silver thiosulfate complex in an aqueous solution, hexagonal column crystals of 100 nm more or less, are formed for the standing time of 3 minutes after dropping it onto a phosphor bronze plate, where it is confirmed that irregularities of several nm order are found on the hexagonal column quantum crystals from the SEM images (FIGS. 4, 5 and 6) and any specific facets derived from a metal nano-crystals are not found, while the EDS elemental analysis shows silver and elements derived from the complexing ligand. Accordingly, it can be estimated from the above analysis that the whole particles show nano-crystals of silver complex and also the unevenness appearance on the surface may be caused by the formation of spread quantum dots made of silver clusters in the complexes. From the aspect of phenomenon that the silver complex quantum crystals of the present invention can be formed on a phosphor bronze plate, while silver nano-particles alone can be deposited on the copper substrate, it is estimated that, as the equilibrium potential of the silver thiosulfate complexes is 0.33 which is equivalent to the copper electrode potential with 0.34, there is deposited only silvers with 0.80 on the copper substrate. On the other hand, in case of a phosphor bronze plate with the electrode potential of 0.22, which is slightly less noble than the copper, so that silver complex crystals seem able to be precipitated. The concentration of the silver complex in the aqueous solution should be in a dilute region of 500~2000 ppm, 2) the electrode potential of the metal substrate with respect to the equilibrium potential of the metal complex solution is slightly less noble, 3) the metal complex should be deposited by the electrode potential difference between the metal substrate and the metal complex. Further, in case of 1000 ppm of thiourea silver complex in aqueous solution, the same function was can be observed.

A substrate of silver thiosulfate quantum crystal made on the phosphor bronze plate in the above example was prepared and, on this substrate an aqueous solution of sodium hypochlorite having pH11 was dropped. After dropping of the aqueous solution, the solution was allowed to stand on the substrate for three minutes and is subsequently blown off to prepare a bio-chip for SERS. On the other hand, the serums obtained from 12 cases of gastric cancer patients, the serum obtained from 12 cases of the colorectal carcinoma patients and the serum obtained from 12 cases of benign disease patients, all of them are diluted 10 times to prepare testing samples, which are subjected to a measurement of Raman spectra with irradiated with 633 nm laser light. There are observed much correlation between the degree of progress and the peak rise values as well as the peak integral value in case of gastric cancer and colon cancer. In addition, in the case of gastric cancer, the peak became to develop in the Raman spectrum developed after one minute of the laser irradiation, the peak became to develop in the Raman spectrum after 2-3 minutes after laser irradiation in the case of colon cancer. Also, D is a graph showing a comparison of the Raman scattering peak rising values concerning gastric cancer, colon cancer and benign disease. The peak of the gastric cancer samples and colon cancer samples are found to be significantly higher than that of. the benign disease samples. While it is difficult to find the difference between the gastric cancer sample and the colon cancer samples concerning the peak rise value, it is possible to identify both cancers considering the peak expression times and the peak integral value.

Figure 12:
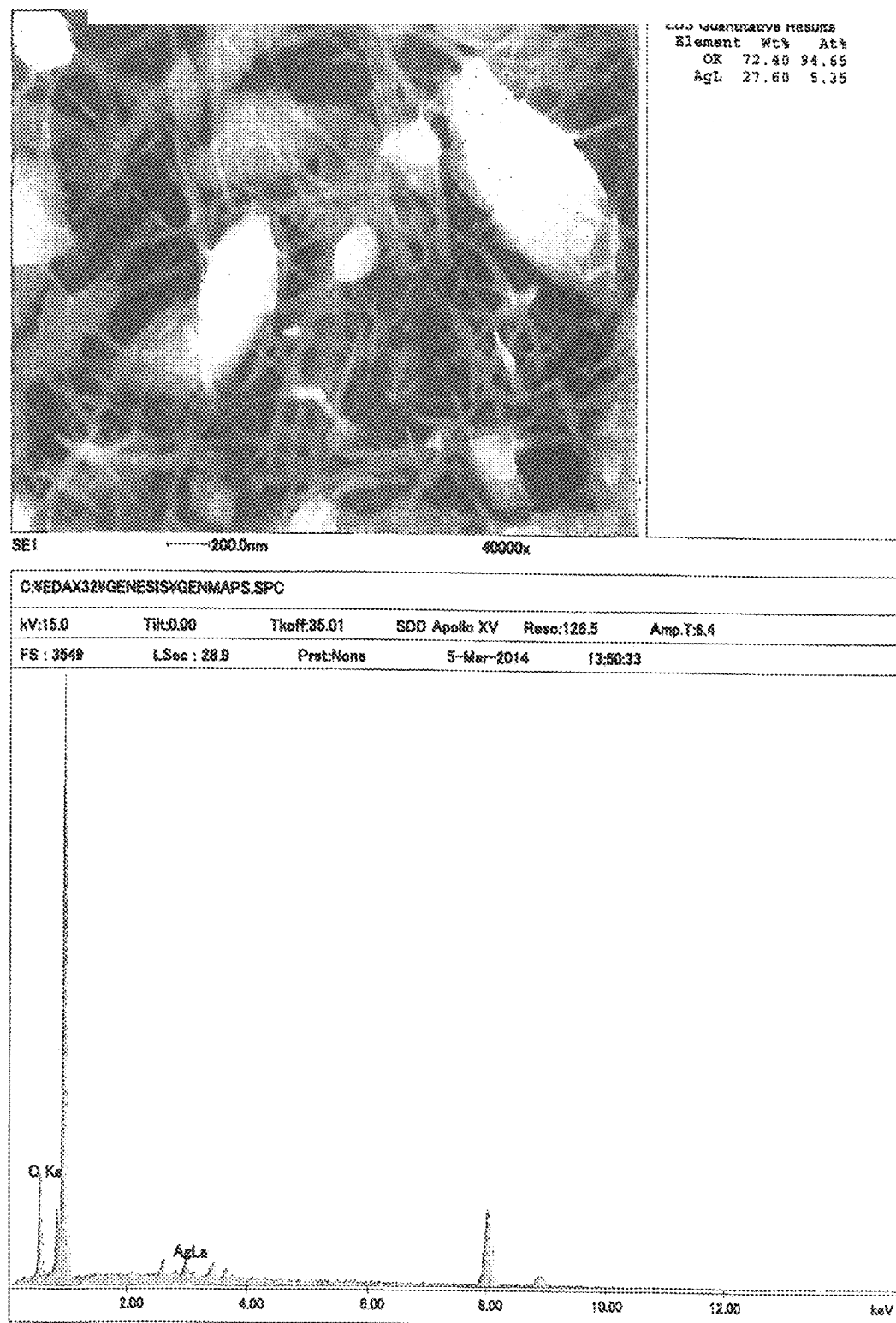
FIG. 12 is a view (top) of SEM image showing a re-crystallized substrate which is the quantum crystal substrate alkali treated in the presence of a halogen ion (sodium hypochlorite treatment) (top view) and a graph (below) showing a result (elemental analysis) of the EDS spectra of the re-crystallized substrate.
Figure 13:
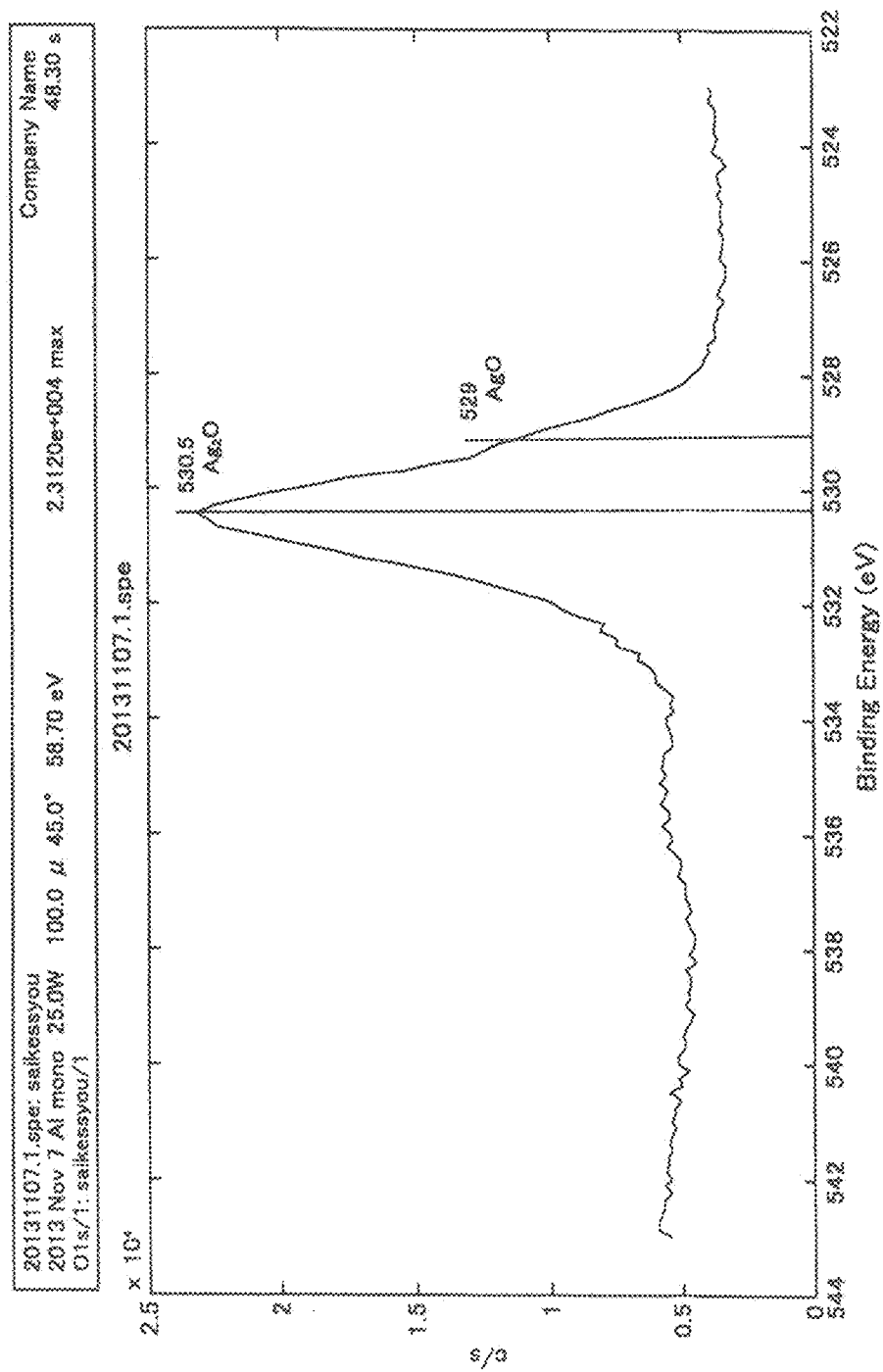
FIG. 13 is a graph showing a result of XPS measurement of the alkali-treated recrystallization substrate.

The quantum crystal substrate is subjected to a treatment of dropping 5% sodium hypochlorite solution thereon and the dropped solution is removed off 2 minutes later to obtain crystals having structures shown in FIG. 12, where needle-shaped crystals and large clumps such as rugby ball-like mass are observed and the respective compositions are subjected to analyzation at EDS spectra (elemental analysis). After a result of the analysis, the needle-like crystals are both considered to consist of a composite crystal of silver oxide and silver chloride, from the following reaction formulas and the result of FIG. 12 does not show any chlorine and shows that the silver and oxygen is dominant.

$$Na_2S_2O_3 + 4NaClO + H_2O \rightarrow Na_2SO_4 + H_2SO_4 + 4NaCl \tag{1}$$

$$Ag^+ + NaCl \rightarrow AgCl + Na^+ \tag{2}$$

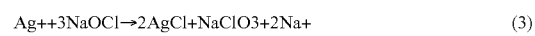
$$Ag^+ + 3NaOCl \rightarrow 2AgCl + NaClO_3 + 2Na^+ \tag{3}$$

$$Ag^+ + OH^- \rightarrow AgOH \tag{4}$$

$$2Ag^+ + 2OH^- \rightarrow Ag_2O + H_2O \tag{5}$$

Thus, although it is considered that silver ions and thiosulfate ions are important in the formation of meso-crystal according to the present invention by alkaline oxidation reaction in the presence of chloride ions and, although the silver oxide is formed according to a conventional reaction, it is surprised that silver peroxide are predominantly formed from the following XPS measurement.

Figure 14:
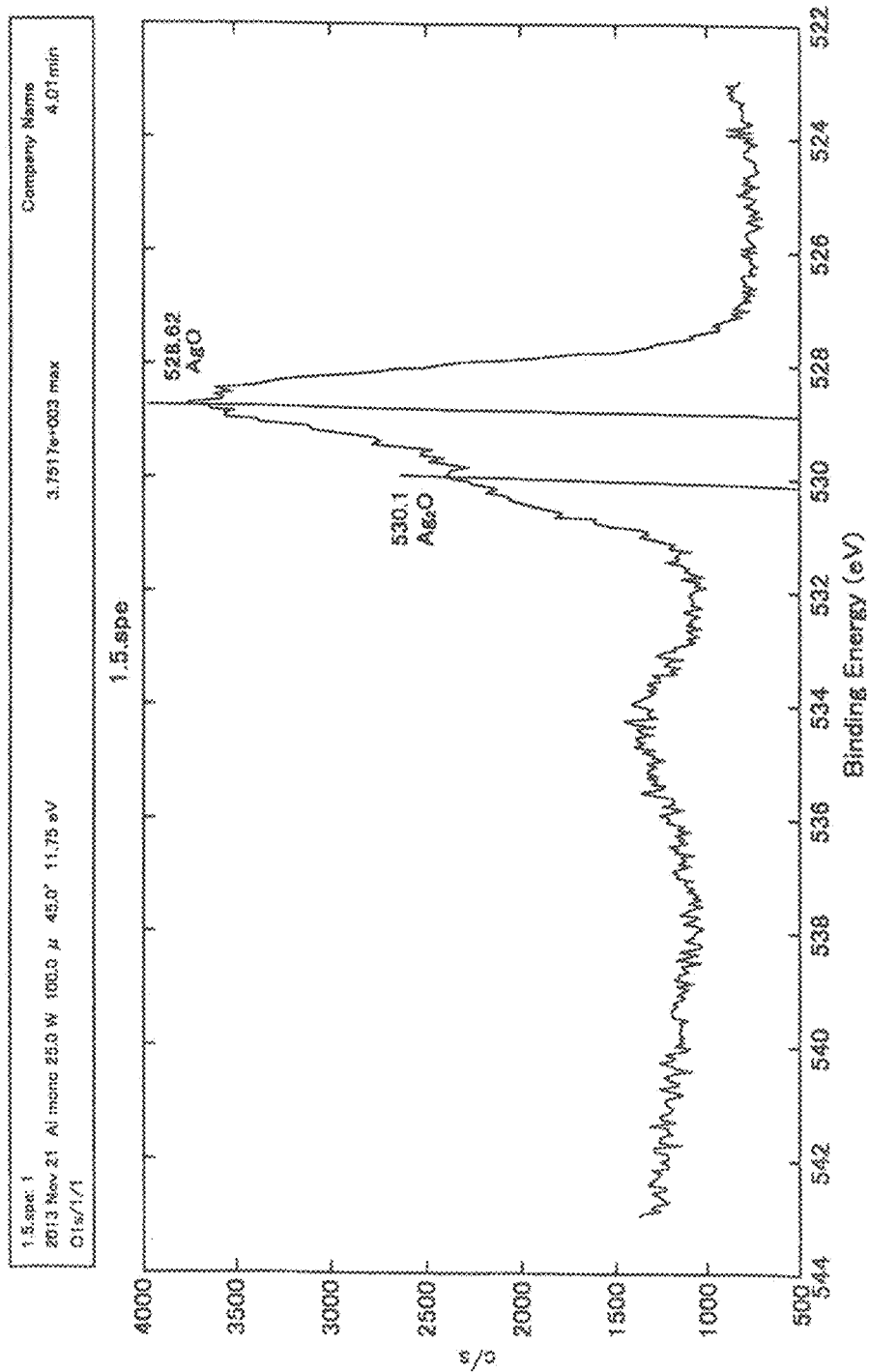
FIG. 14 is a graph showing a result of XPS measurements after etching the surface of the recrystallization substrate.

XPS measurement: The aqueous sodium hypochlorite was added dropwise to the quantum crystal substrate prepared as the above for 2 minutes, to make a re-crystal substrate, which is subjected to a XPS analysis (using models: ULVAC-PHI (Ltd.)/PHI5000 Versa Probe II (scanning X-ray photoelectron spectroscopy) without etching for Ag and O by XPS measurement. In addition, for comparison, Ag in the powder of silver chloride and the powder of silver oxide were measured. On the other hand, the recrystallized substrate was subjected to XPS measurement of Ag and O after etching for 5 minutes with an argon gas cluster ion gun. If the XPS measurement results of FIGS. 13 and 14 will be combined with the results of EDS according to FIG. 12, the peak in the vicinity of 529 eV is the peak derived from silver peroxide (AgO), while the peak in the vicinity of 530 eV is the peak derived from silver oxide (Ag2O). Further, If it is etched, the oxygen content decreases, while the 0 peak derived from the silver peroxide (AgO) in the vicinity of 529 eV is still greater than the peak derived from the silver oxide in the vicinity of 530 eV in case of etching, so that it is recognized that the silver peroxide was produced in the vicinity of the substrate. It is assumed that the electrode potential of the substrate and the catalytic action are affected. to the meso-crystal formation. The EDS measurement was carried on the above-mentioned re-crystal substrate by using a JEOL Ltd./JSM-7001F (field emission scanning electron microscope analysis).

In addition, if the aqueous solution is selected from the group consisting of hypochlorous acid, 0.01 N sodium hydroxide, 0.01 N hydrochloric acid and 0.1 molar sodium carbonate, any result similar to treatment with sodium hypochlorite was not obtained. Thus, it is believed that the formation of the needle-like crystals is caused by the above reaction in the presence of silver ions and thiosulfate ions. While the silver oxide is induced into negative charge in an aqueous solution, it is reduced by the light to deposit metallic silver. Since silver peroxide shows more remarkably in the above tendency than silver oxide, it is possible to adsorb cancer related substances having a positive charge, resulting in occurrence of the surface plasmon enhancement effect between the trapped cancer-related substance and the silver particles.

Thus, according to the present invention, it is possible to selectively detect cancer related substances in the blood and biological samples, so that the early detection of cancer and the judgement of progress of cancer can be made by the measurement of Raman spectra.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents.

What is claimed is:

1. A method of measuring a quantity of cancer related substances by Surface Enhanced Raman Scattering (SERS), the method comprising the steps of preparing a biochip having a meso-crystal region of silver oxides containing a silver peroxide, adding dropwise a serum or biological liquid sample to the meso-crystal region of the biochip, selectively trapping cancer related substance having a positive charge in the sample, irradiating the trapped cancer related substance with an exciting light, and detecting the surface enhanced Raman scattering light.

2. The method of claim 1, wherein the detected Raman scattering spectrum shows carbon inherent peaks in the zone of D band and G band and a characteristic peak in the vicinity of 2900 $cm^{-1}$ as spectrum of the cancer related substances.

3. The method of claim 2, wherein the cancer related substance contains a released DNA (DNA wrapped around the histones: nucleosomes), and the relevant chromatin (chromosome).

* * * * *